United States Patent [19]

Mason, Jr. et al.

[11] 4,391,799

[45] Jul. 5, 1983

[54] PROTECTIVE GEL COMPOSITION FOR TREATING WHITE PHOSPHORUS BURN WOUNDS

[75] Inventors: Arthur D. Mason, Jr.; Avery A. Johnson, Jr., both of San Antonio, Tex.; Charles R. Ritchey, Stillwater, Okla.

[73] Assignee: The United States of America as represented by the Secretary of the Army, Washington, D.C.

[21] Appl. No.: 316,575

[22] Filed: Oct. 30, 1981

Related U.S. Application Data

[63] Continuation of Ser. No. 121,870, Feb. 15, 1980, abandoned.

[51] Int. Cl.$^3$ ............................................. A61K 33/38
[52] U.S. Cl. ..................... 424/132; 424/141; 424/143; 424/290; 424/364; 424/DIG. 13
[58] Field of Search ............... 424/132, 140, 141, 143, 424/DIG. 13

[56] References Cited

U.S. PATENT DOCUMENTS

| | | | |
|---|---|---|---|
| 2,338,416 | 1/1944 | Fales | 424/DIG. 13 X |
| 2,405,861 | 8/1946 | Tod | 252/316 |
| 2,845,381 | 7/1958 | Tindall | 424/DIG. 13 X |
| 3,639,575 | 2/1972 | Schmolka | 424/132 |

OTHER PUBLICATIONS

Gooding et al., Journal of the American Medical Assoc., (1942), p. 1059.
Stadlinger; Chemical Abstracts, vol. 39, p. 2587, "Treatment of Phosphorus Burns".
Lachman et al., The Theory & Practice of Industrial Pharmacy, 2nd ed., (1976), pp. 229-230.

*Primary Examiner*—Leonard Schenkman
*Attorney, Agent, or Firm*—William G. Gapcynski; Werten F. W. Bellamy; Jack M. Petruncio

[57] ABSTRACT

Water soluble hydrogels of alkali metal alginate and glycerin containing 0.01 to 1% cupric (copper) sulfate pentahydrate or silver salts such as silver acetate, silver lactate monohydrate and silver nitrate have been found to be excellent wound dressing treatment composition for white phosphorus burns.

Cupric sulfate pentahydrate or silver salts such as silver acetate, silver lactate monohydrate and silver nitrate in the gel reacts with the particles of white phosphorus to form a coating around said particles thus rendering them unable to cause further burn injury to the skin. The gels dry to an adherent, non-toxic pliable protective film which can be removed by water-washing when desired. The gels are also compatible with other medicaments and hence can serve as vehicles or carriers for medicament application to wounds as well as a protective cover.

4 Claims, No Drawings

PROTECTIVE GEL COMPOSITION FOR TREATING WHITE PHOSPHORUS BURN WOUNDS

This is a continuation of application Ser. No. 121,870, filed Feb. 15, 1980, now abandoned.

BACKGROUND OF THE INVENTION

1. Field of the Invention

This invention relates to novel water soluble hydrogel compositions of alkali metal alginate and glycerin containing 0.01 to 1% cupric sulfate pentahydrate or silver nitrate and their use in the protection and treatment of white phosphorus burns. More particularly, the invention is directed to water-soluble gel compositions which dry to a pliable film which makes them especially suited for use as white phosphorus wound dressings wherein the cupric sulfate or silver salt such as silver acetate, silver lactate monohydrate and silver nitrate in the gel reacts with the particles of white phosphorus to form a coating around the particles.

2. Brief Description of the Prior Art

Gel preparations and protective films of various types are known and have been employed for the treatment of surface wounds. For example, U.S. Pat. No. 3,949,742 to B. Nowakowski, discloses a transparent medical dressing comprised of a laminate of a thin layer of non-porous segmented polyurethane cohesively secured to a thin layer of thrombogenic reticulated foam. The medical dressing is permeable to gases but impermeable to liquids and bacteria and performs as a synthetic film over skin wounds.

U.S. Pat. No. 3,880,158 to A. Gurney discloses a composition comprised of a mixture of non-elastomeric and elastomeric block polymers in an aerosol container which can be sprayed over a wound to form a fibrous bandage thereover.

U.S. Pat. No. 3,879,168 to K. J. Franklin discloses a surgical dressing made of partially soluble alginic material in the form of gauze or wool characterised by a pH of 4 to 7 and a calcium content of 2-6% by weight.

U.S. Pat. No. 3,639,575 to Schmolka discloses the use of silver ion gel compositions, including silver nitrate immersed in an aqueous gel of certain polyoxyethylene polyorypropylene block copolymers, for the purpose of treating burns.

U.S. Pat. No. 3,761,590 to Fox discloses a silver sulfadiazine-containing ointment used to treat burns. The ointment includes a water-dispersible, hydrophilic carrier.

U.S. Pat. No. 3,902,552 to Romans discloses the use of silver nitrate as an ingredient in an antiseptic ointment.

The article appearing in *Handbook of Dangerous Materials*, by Irving Sax, Rheinhold Publishing Corporation, New York, 1951 discloses a 3% aqueous solution of copper sulfate for the treatment of phosphorus burns.

The article appearing in *British Medical Journal*, London, 1:429-458 (April, 14, 1942) entitled "Treatment of Phosphorus Burns" by Godding and Notton discloses the use of copper sulfate-glycerin paste in treating burns.

While previous attempts to formulate hydrogel compositions such as those described above may protect wounds satisfactorily, they are not without their shortcomings.

When white phorphorus is exposed to air, it ignites and burns. Thus, if white phosphorus particles come in contact with the skin and are left untreated, serious burns are inflicted. Moreover, so long as air can reach the white phorphorus particles, they will continue to burn thereby causing more extensive injury to the victim.

Some attempts have been made to treat white phosphorus burns with certain compositions referred to as "wet dressings." However, the use of the gel composition of the instant invention overcomes the many disadvantages associated with the conventional "wet dressings." Wet dressings commonly consist of a mixture of water and medicaments for treating the burn wound. If the wet dressings are allowed to dry, the white phosphorus will reignite causing further injury. Additionally, the wet dressings suffer from the disadvantages which include (1) exacerbation of the hypermetabolic state by increasing caloric deficit and heat loss, (2) loss of plasma water, serum protein, and serum electrolytes, (3) maceration of burn wound surfaces, (4) increase of the fluid loss by vaporization, (5) extensive nursing care and (6) economic loss due to discoloration of bedding, equipment, floors, and walls. With so many disadvantages it is little wonder that artisans continue their search for alternative methods of treating burns. While some limited success has been achieved in this area, the present invention discloses for the first time a novel gel composition with superior adhesive and flexibility properties which contains effective quantities of medicaments which encapsulates the white phosphorus burn wound, prevents autoignition of the white phosphorus by exposure to air and protects the wound against invasion by bacteria. Operatively, the encapsulating medicament i.e., silver or copper ions react with the phosphorus particles in the wound causing them to darken. The darken so white phosphorus particles can be easily seen by the surgeon and removed.

In all cases, prior art wound-covering compositions or antidotes for treating white phosphorus are deficient in one or more of the characteristics desired in compositions set out below under the Objects of the Invention.

OBJECTS OF THE INVENTION

It is an object of the present invention to provide an alkali metal alginate and glycerin gel composition containing a silver salt such as silver acetate, silver lactate monohydrate and silver nitrate or copper sulfate pentahydrate suitable as protective-antidote compositions in the treatment of white phosphorus burn wounds. These gel compositions will dry in air to form a tightly adherent flexible film over the burn wound area.

Another object of the invention is to provide a wound dressing content which when dry provides a transparent film that prevents bacteria or air from reaching the wound.

Yet another object of the invention is to provide a material which can be easily applied over wounds in gel form and dried into a water-soluble film which can be removed from the wound by simple water-washing.

A further object of the invention is to provide a cheap and stable composition which is compatible with medicaments such as silver acetate, silver lactate monohydrate, silver nitrate or copper sulfate pentahydrate and can therefore serve as a carrier or vehicle for applying medicaments to white phosphorus burn wounds.

An additional object is to provide a composition which can be applied as a film over a previously applied layer or layers of the same composition without first removing the deeper layers.

Another object is to provide a novel method for protecting and treating white phosphorus surface wounds.

SUMMARY OF THE INVENTION

These and other objects of the invention are obtained by a gel composition comprising a water-soluble hydrogel of an alkali metal alginate and glycerin. In the preferred embodiment of this invention, a medicament such as silver acetate, silver lactate monohydrate, silver nitrate or copper sulfate pentahydrate is dispersed throughout the water-soluble hydrogel. However, other water-soluble silver salts which may be employed in the preparation of the gels of the present invention are those silver salts which will dissolve in water at a minimum concentration of 0.1% by weight of silver salt based on the weight of the water in the gel.

In accordance with the method of the invention, wounds are protected and treated by applying over the white phosphorus burn wound surface a coating of the novel gel compositions and drying the coating to a water-soluble, flexible film.

The preferred gel compositions of the invention may be prepared by simply stirring in water, alkali metal alginate, glycerin and at least one medicament such as silver nitrate, silver acetate, silver lactate monohydrate, or copper sulfate pentahydrate until a gel is formed. The order of addition is not critical but it is preferred to first stir in the alkali metal alginate and then glycerin. The medicament is preferably added after solution of the alkali metal alginate and glycerin or alternatively, after the alkali metal alginate and glycerin have formed a gel. Any suitable stirring means can be used to form the gel but best results are obtained with a mechanical homogenizer. The preferred alkali metal alginate of the invention is sodium alginate.

The proportions of alkali metal alginate, glycerin and water may vary depending upon the properties of the materials used and the particular use to which the composition will be put but in all instances, the components will be employed in hydrogel-forming proportions. In general, the hydrogel comprises about 0.5 to 3% by weight alkali metal alginate, about 8 to 12% by weight glycerin and about 82 to 90% by weight water. Advantageously, the proportions of gel components are selected so as to form a hydrogel having a pH in the range of 6.8 to 7.2 since a pH in this range is found to provide storage stable compositions.

Medicaments in addition to the silver salts or copper sulfate pentahydrate which can be incorporated in the novel gels of the invention include for instance, biocidal agents such as antibiotics, and bactericides; chemotherapeutic agents; drugs and the like. The concentrations of medicaments in the composition when employed will vary depending upon the particular medicament employed but in all instances will be an amount effective for its intended purpose. In general, the total amount of medicaments in the compositions of the invention will range from about 0.01 to 10% by weight. However, the amount of the silver salt or copper sulfate pentahydrate medicament is in the range of 0.01 to 1%.

Surprisingly, we have found that small quantities of either cupric sulfate pentahydrate ($CuSO_4.5H_2O$) or silver nitrate ($AgNO_3$) may be added to the alkali metal alginate-glycerin hydrogel compositions described herein to formulate a very effective antidote for the treatment of white phosphorus burns. The cupric sulfate pentahydrate or silver salts in the hydrogel react with the particles of white phosphorus to form a coating which encapsulates the phosphorus and thus prevents its burning. Additionally, the hydrogel composition prevents air from coming in contact with the white phosphorus and igniting it before the encapsulating coating is formed. The hydrogel composition not only serves as a vehicle for the cupric sulfate or silver salts, but it also serves as a barrier to outside bacterial invasion of the wound. The encapsulated particles in the burn wound stand out against the background as vivid black particles. Since the antidote hydrogel composition remains in contact with the white phosphorus, a much lower concentration of cupric sulfate or silver nitrate is required as compared to an aqueous solution containing these chemical medicaments. For example, we have demonstrated that a 0.1% cupric sulfate pentahydrate hydrogel composition rapidly darkens a piece of white phosphorus and that even a 0.01% cupric sulfate hydrogel composition will darken it at a slower rate. Prior art teachings suggest 1 to 3% aqueous solutions of silver nitrate or cupric sulfate in treating phosphorus burn wounds as compared to incorporating effective quantities of medicatives as low as 0.01 to 0.1% in the hydrogel compositions of the instant invention. This quantitative difference is especially significant in the case of cupric sulfate pentahydrate due to its toxic nature.

The gel compositions of the invention are easily manipulated jelly materials and can be applied to a body surface by brush, applicator or any other of a variety of means. The applied gel coating has been found to dry on exposure to air at ambient temperature and form a nontoxic, transparent, flexible and stretchable film which is tightly adherent to the body surface. Thus, the film is useful in the protection of wounds from infection by organisms in the environment and from further injury by external agents. Its ability to stretch and bend without tearing or disturbing adherence to the wound enables it to be used over joints of human and animal bodies.

A particularly advantageous characteristic of compositions of the invention resides in the fact that they are water-soluble. Hence, dried film-coatings of the compositions can be removed when desired by a simple waterwash. In addition, reapplication of the composition over a previously applied area can be made without removing underlying layers of the composition.

The transparency of the composition of the invention enables one to observe the wound underneath and remove the vivid black encapsulated phosphorus particles from the wound.

The following examples are illustrative, without implied limitation, of our invention.

EXAMPLE 1

12.5 grams of sodium alginate is slowly added with constant stirring to 400 milliliters of water at room temperature. After the sodium alginate has been added and has formed a thick solution, 50 milliliters of glycerin is stirred in. As an aid toward obtaining a homogeneous solution, the aqueous glycerin-sodium alginate solution is homogenized using a VirTis "45" homogenizer. A gel with a pH of 7.0 is obtained which is stable when kept in a tightly closed container.

EXAMPLE 2

Ten (10) milliliters of an aqueous silver nitrate solution containing 0.13 grams of silver nitrate is added slowly with homogenization to 53 grams of the glycerin-sodium alginate gel of Example 1.

EXAMPLE 3

Five (5) grams of sodium alginate is stirred into 200 milliliters of water after which 20 milliliters of glycerin is stirred in. Following solution of the sodium alginate and glycerin, 2-5 grams of sulfamylon (mafenide acetate) is stirred in and the resulting solution homogenized.

The following Example 4 illustrates the protection offered by the gel compositions of the invention.

EXAMPLE 4

Fifteen (15) 200 gm, male, Holtzman rats were burned over 20% of total body surface by 10 second exposure to 100° C. water. Nine (9) animals were selected at random for application of the gel of Example 1; six (6) were not treated. After 24 hours, each burn wound was seeded with approximately $10^8$ colony forming units of Pseudomonas aeruginosa, ISR strain 8-28-3 (63); this dose was applied to the gel surface in the treated animals and to the burn surface in the untreated animals. The animals were then observed for 30 days, with daily reapplication of the gel to the burn wounds of the treated animals for the first 10 days of the observation period. Results were as shown in the following table.

| GROUP | POSTBURN DAY OF DEATH | NO. DEATHS | NO. ANIMALS |
|---|---|---|---|
| Treated | 17 | 1 | 9 |
| Control | 9,9,10,11,14 | 5 | 6 |

EXAMPLE 5

To an alginate gel containing 1674 grams of water, 9 grams sodium alginate, and 26 grams of glycerin, 57 grams of an aqueous solution containing 2 grams of cupric sulfate pentahydrate was slowly added. The resulting gel was then homogenized using a Vir-Tis 45 homogenizer.

EXAMPLE 6

To an alginate gel containing 1674 grams water, 9 grams sodium alginate, and 26 grams glycerin, 57 grams of an aqueous solution containing 1.4 grams of silver nitrate was slowly added. The resulting gel was then homogenized using a Vir-Tis 45 homogenizer.

We claim:

1. A method for treating white phosphorus burn wounds which comprises applying over the wound surface a coating of an aqueous gel composition comprising 0.01 to 1% by weight of a water-soluble silver or copper salt selected from the group consisting of silver nitrate, silver acetate, silver lactate monohydrate and copper sulfate pentahydrate which will dissolve in water at a minimum concentration of 0.1% by weight of the water in the gel and as a matrix therefor, a water-soluble hydrogel consisting essentially of about 0.5 to 3% by weight alkali metal alginate, about 8 to 12% by weight glycerin and about 82 to 90% by weight water wherein the hydrogel has a pH in the range of 6.8 to 7.2 and which upon drying forms a flexible, stretchable, transparent, water-soluble protective film, non-toxic and adherent to a white phosphorus burn wound surface to which gel composition is applied, and which allows for encapsulation and removal of vivid darkened white phosphorus particles.

2. A method of claim 1 wherein the silver salt is silver nitrate.

3. A method of claim 1 wherein the copper salt is 0.01% to 0.1% copper sulfate pentahydrate.

4. A method of claim 1 wherein the gel composition comprises a medicament in addition to said water soluble silver or copper salt.

* * * * *